US 11,189,364 B1

(12) United States Patent
Shaw et al.

(10) Patent No.: US 11,189,364 B1
(45) Date of Patent: Nov. 30, 2021

(54) COMPUTING PLATFORM FOR ESTABLISHING REFERRALS

(71) Applicant: IQVIA Inc., Danbury, CT (US)

(72) Inventors: Katie Shaw, Apex, NC (US); Davie Yang, Morrisville, NC (US); Leonard Bishop, Fuquay-Varina, NC (US); Kimberly Ray, Atlanta, GA (US); Timothy Riely, Raleigh, NC (US); Lucas Glass, Devon, PA (US); Patrick Lample, Paris (FR); Susan Warne, Houston, TX (US)

(73) Assignee: IQVIA Inc., Parsippany, NJ (US)

( * ) Notice: Subject to any disclaimer, the term of this patent is extended or adjusted under 35 U.S.C. 154(b) by 176 days.

(21) Appl. No.: 15/914,653

(22) Filed: Mar. 7, 2018

(51) Int. Cl.
| | |
|---|---|
| *G16H 10/20* | (2018.01) |
| *G16H 50/70* | (2018.01) |
| *G16H 80/00* | (2018.01) |
| *G16H 50/20* | (2018.01) |
| *G06N 20/00* | (2019.01) |

(52) U.S. Cl.
CPC ............. *G16H 10/20* (2018.01); *G06N 20/00* (2019.01); *G16H 50/20* (2018.01); *G16H 50/70* (2018.01); *G16H 80/00* (2018.01)

(58) Field of Classification Search
CPC ........ G16H 10/20; G16H 50/70; G16H 50/20; G16H 80/00; G06N 20/00
USPC .......................................................... 705/2
See application file for complete search history.

(56) References Cited

U.S. PATENT DOCUMENTS

| | | | |
|---|---|---|---|
| 7,401,028 B2 | 7/2008 | Deakter | |
| 9,460,400 B2* | 10/2016 | De Bruin | ................. A61B 5/00 |
| 10,998,101 B1* | 5/2021 | Tran | ..................... A61B 5/0205 |
| 2003/0065669 A1 | 4/2003 | Kahn et al. | |
| 2004/0078216 A1* | 4/2004 | Toto | ........................ G16H 10/60 |
| | | | 705/2 |
| 2004/0243439 A1* | 12/2004 | Huggard | ................ G06Q 10/10 |
| | | | 705/2 |
| 2005/0071189 A1* | 3/2005 | Blake | ..................... G06Q 10/10 |
| | | | 705/2 |
| 2005/0159986 A1* | 7/2005 | Breeland | ................ G16H 10/60 |
| | | | 705/3 |
| 2005/0182663 A1* | 8/2005 | Abraham-Fuchs | .... G06Q 10/10 |
| | | | 705/3 |

(Continued)

*Primary Examiner* — Michael Tomaszewski
*Assistant Examiner* — Rachael Sojin Stone
(74) *Attorney, Agent, or Firm* — Fish & Richardson P.C.

(57) ABSTRACT

Methods, systems, and apparatus, including computer programs encoded on a computer storage medium, for a computing platform that identifies information about a trial program, where the information is related to healthcare data included in datasets, and identifies an investigator based on the information about the trial program. A data analytics model of the platform generates an initial provider score for each provider in a group of providers based on analysis of the information. The analyzed information of the datasets includes healthcare data describing interactions between patients and providers in the group and criteria for the trial program. The platform provides a request to a subset of providers using the initial provider scores. The request is an invitation to for each provider to join a referral network. The platform uses the request to establish referral connections between the trial investigator and a provider in the subset.

20 Claims, 5 Drawing Sheets

(56) References Cited

U.S. PATENT DOCUMENTS

| | | | |
|---|---|---|---|
| 2005/0234740 A1* | 10/2005 | Krishnan | G06Q 10/06398 |
| | | | 705/2 |
| 2006/0080146 A1* | 4/2006 | Cook | G06Q 10/00 |
| | | | 705/2 |
| 2008/0010254 A1* | 1/2008 | Settimi | G06Q 10/06 |
| 2009/0313045 A1 | 12/2009 | Boyce | |
| 2010/0088245 A1 | 4/2010 | Harrison et al. | |
| 2010/0332258 A1 | 12/2010 | Dahlke et al. | |
| 2011/0301982 A1 | 12/2011 | Green et al. | |
| 2012/0158420 A1 | 6/2012 | Lacal | |
| 2012/0296662 A1* | 11/2012 | Bailey | G06Q 50/22 |
| | | | 705/2 |
| 2013/0096942 A1* | 4/2013 | Bowles | G06Q 50/22 |
| | | | 705/2 |
| 2013/0332190 A1 | 12/2013 | Hoffman et al. | |
| 2013/0332191 A1 | 12/2013 | Hoffman et al. | |
| 2013/0346104 A1 | 12/2013 | Pillai | |
| 2014/0046926 A1 | 2/2014 | Walton | |
| 2014/0136237 A1* | 5/2014 | Anderson | G16H 10/60 |
| | | | 705/3 |
| 2014/0207492 A1* | 7/2014 | Farooq | G16H 40/20 |
| | | | 705/3 |
| 2014/0236623 A1 | 8/2014 | Shiovitz | |
| 2014/0244309 A1* | 8/2014 | Francois | G06Q 10/10 |
| | | | 705/3 |
| 2014/0278511 A1* | 9/2014 | Fielding | G06Q 10/10 |
| | | | 705/2 |
| 2014/0316793 A1 | 10/2014 | Pruit | |
| 2015/0161336 A1 | 6/2015 | Kalathil | |
| 2016/0004820 A1 | 1/2016 | Moore | |
| 2017/0061102 A1* | 3/2017 | Weber | G06Q 50/01 |
| 2017/0199189 A1 | 7/2017 | Wade | |
| 2018/0119137 A1* | 5/2018 | Matsuguchi | C12Q 1/6827 |
| 2018/0232659 A1* | 8/2018 | Ranatunga | G06Q 30/02 |
| 2020/0225655 A1* | 7/2020 | Cella | G06N 3/0472 |
| 2020/0381086 A1* | 12/2020 | Atreja | G16H 15/00 |
| 2021/0118559 A1* | 4/2021 | Lefkofsky | G16H 50/20 |

* cited by examiner

COMPUTING PLATFORM FOR ESTABLISHING REFERRALS

FIELD

This specification relates to predictive computing platforms.

BACKGROUND

As part of the health care process, physicians or other medical care providers may perform clinical trials, programs, and other activities to evaluate the subject safety and efficacy of a pharmaceutical drug or other medical treatment option. The use of health-related trial programs can help to identify novel treatment options for improving overall patient health and reducing health system costs. For the purposes of gaining approval of particular treatment option, a clinical trial or program can be a research study that prospectively assigns human participants/subjects or groups of human subjects to one or more health-related interventions to evaluate the effects on health outcomes.

The effectiveness of a program can depend on the availability of subjects or patients that are suitable for enrollment and participation in the program. Traditional patient or subject enrollment techniques leverage mass media direct to patient campaigns and leverage principal investigators that are responsible for executing the program to recruit patients. However, execution of clinical trials and other controlled programs may be delayed due to challenges in identifying and recruitment suitable subjects for participation in the program. In some instances, controlled programs are sometimes unable to enroll subjects for participation the program. In other instances, principal investigators and geographic site locations may miss enrollment targets due to the limited resources for developing and engaging existing subject networks that include suitable subjects for enrollment in a particular program.

SUMMARY

As part of the health care process, physicians or other medical care providers may perform trials, programs, and other activities to evaluate the efficacy of a particular pharmaceutical drug or other medical treatment option. Conducting health-related clinical trials can help to identify medical treatment options for improving overall patient health and reducing health system costs. Clinical trials and other controlled programs are generally conducted by investigators that use a particular geographic site location(s) to interact with study subjects and execute process steps for conducting the program. An investigator, a geographic site location, or both, can form an entity that executes a program. The effectiveness of a program can depend on the availability of subjects or patients that are suitable for enrollment and participation in the program.

In the context of identifying patients for enrollment in a trial program, systems and methods are described for a computing platform that identifies information about a trial program, where the information is related to healthcare data included in datasets, and identifies an investigator based on the information about the trial program. A data analytics model of the platform generates an initial provider score for each provider in a group of providers based on analysis of the information. The analyzed information of the datasets includes healthcare data describing interactions between patients and providers in the group and criteria for the trial program. The platform provides a request to a subset of providers using the initial provider scores. The request is an invitation for each provider to join a referral network. The platform uses the request to establish referral connections between the trial investigator and a provider in the subset. The connection is established in response to the computing system receiving an indication that the provider in the subset accepted the request to join the electronic referral network One aspect of the subject matter described in this specification can be embodied in a computer-implemented method. The method includes, identifying, by a computing system, information about a trial program, the information being related to healthcare data included in datasets; and identifying, by the computing system, a trial investigator based on the information about the trial program. The method includes, generating, by a data analytics model of the computing system, a respective initial provider score for each provider from among multiple providers based on analysis of the datasets, where analyzed information of the datasets includes: healthcare data describing interactions between patients and each of the multiple providers, and a set of criteria for the trial program. The method also includes providing, by the computing system, a request to each provider in a subset of providers based on the respective initial provider scores for providers in the subset, wherein the request represents an invitation to join an electronic referral network; and establishing, by the computing system and based on the request, a referral connection between the trial investigator and a provider in the subset, the referral connection being established in response to the computing system receiving an indication that the provider in the subset accepted the request to join the electronic referral network.

These and other implementations can each optionally include one or more of the following features. For example, in some implementations, generating the respective initial provider score for each provider includes: generating a listing of providers that are identified for participation in the electronic referral network; ranking each provider relative to other providers in the listing based on the respective initial provider score for each provider in the listing; and determining the subset of providers based on a ranking order of each provider in the listing. In some implementations, generating the initial provider score for the provider in the subset includes: generating the initial provider score based on at least one of: a quantity of patients managed by the provider that are eligible for participation in the trial program; the provider's proximity to one or more of multiple trial investigators for conducting the trial program; or a quantity of patients managed by the provider that are shared with one or more of multiple trial investigators for conducting the trial program.

In some implementations, the initial provider score for the provider in the subset that has the referral connection to the trial investigator indicates a likelihood that the provider will identify and refer a patient to the trial investigator that is a suitable candidate for participation in the trial program. In some implementations, wherein the computing system includes a machine learning system, and the method further includes: producing, by the machine learning system, the data analytics model based on a first set of inferences determined from analysis of: i) the healthcare data for each of the multiple providers; and ii) the set of criteria for the trial program; and generating the respective initial provider score for each provider using the data analytics model produced based on the first set of inferences.

In some implementations, the method further includes: producing, by the machine learning system and based on a second set of inferences, a modified data analytics model having enhanced prediction capability; and generating, by the modified data analytics model, a respective adjusted provider score for each provider in the subset of providers using the enhanced prediction capability. In some implementations, the adjusted provider score for the provider in the subset that has the referral connection to the trial investigator indicates: an increased likelihood that the provider will identify and refer a patient to the trial investigator that is a suitable candidate for participation in the trial program; or a decreased likelihood that the provider will identify and refer a patient to the trial investigator that is a suitable candidate for participation in the trial program. In some implementations, the set of criteria for the trial program includes: inclusion criteria for identifying candidate subjects for participating in the trial program; and exclusion criteria for identifying candidate subjects to be excluded from participating in the trial program.

Other implementations of this and other aspects include corresponding systems, apparatus, and computer programs, configured to perform the actions of the methods, encoded on computer storage devices. A computing system of one or more computers or hardware circuits can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The subject matter described in this specification can be implemented to realize one or more of the following advantages. Techniques are described for implementing a referral platform that efficiently establishes referral connections between healthcare entities that interact with potential subjects and investigators that execute trial programs. A computing platform uses a specific set of computer-implemented rules to analyze and processes data describing controlled programs (e.g., clinical trials). Standardized methods for analyzing the data enable the computing platform to identify a healthcare provider that can form a referral relationship with an investigator for referring candidates as subjects for participation in a trial program. For example, the platform can leverage a predictive network model that executes scoring logic to evaluate and identify healthcare providers using a respective generated score for each healthcare provider in a subset of providers. The predictive model continuously analyzes new and existing information to improve efficiency and effectiveness of the scoring, evaluation, and identification process for selecting entities for inclusion in the referral platform.

The described platform enables automation of specific data analytics for generating referral connections between healthcare entities and investigators that previously could not be performed by computer systems in an efficient manner. The described techniques use machine learning to continuously improve upon the scoring logic thereby enabling the platform to identify healthcare providers that are more likely to refer candidates that are suitable subjects for participation in a particular program. A repeatable automated process is provided that involves minimal human intervention and does not require manual execution of business agreements or provider assessments to facilitate establishing effective referral connections between providers and trial investigators. The specific computing rules enable healthcare providers to access a vast array of clinical trial data in order to locate specific trial programs that align with the healthcare needs of their patient base. As such, the described techniques enable a computer to perform operations that the computer was previously unable to perform due to challenges with effectively leveraging different types of healthcare data to automatically and efficiently establish referral connections between different entities and to facilitate subject referrals from a provider to an investigator.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
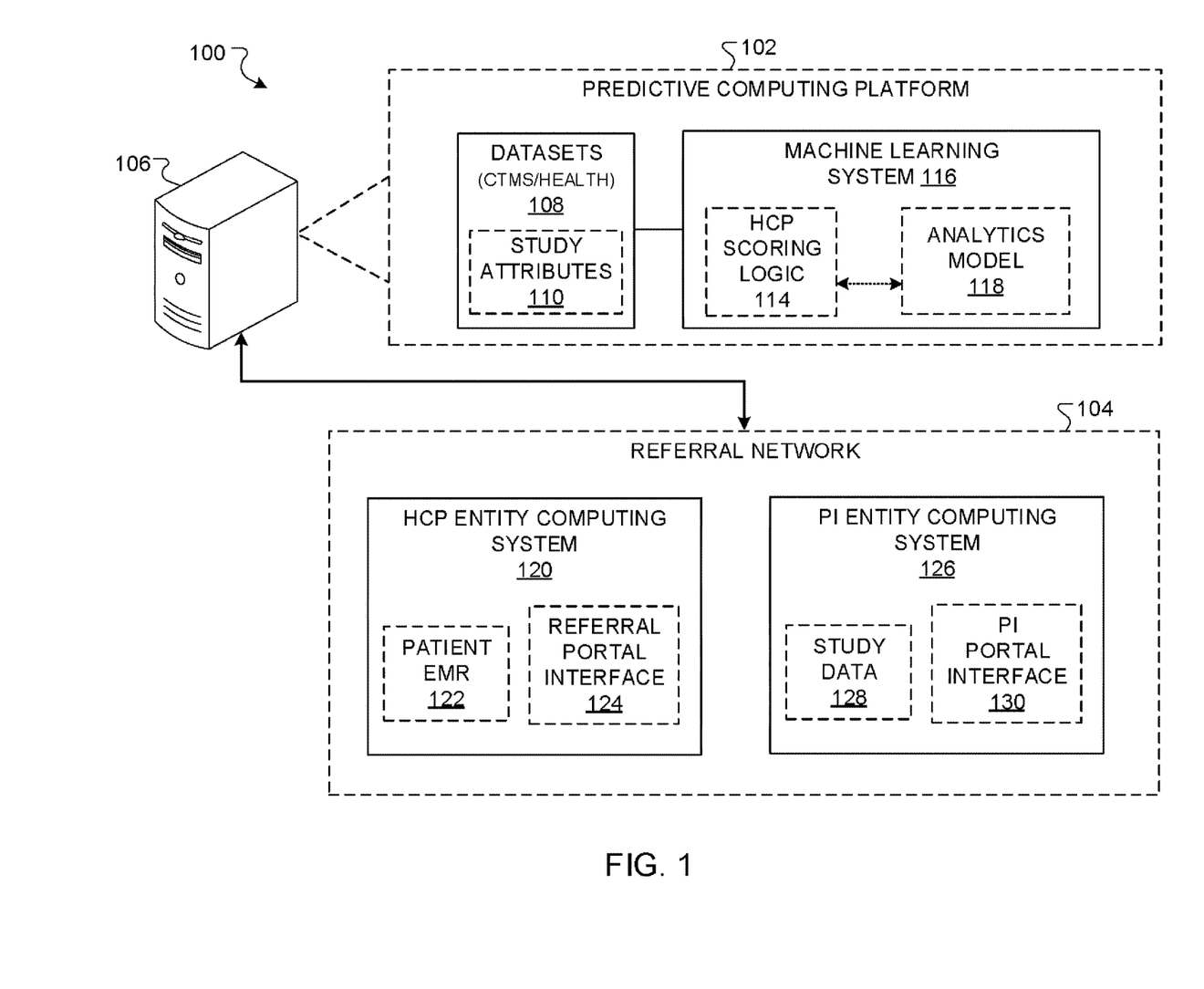
FIG. 1 shows a block diagram of a computing system that includes a computing platform for establishing referral connections within a referral network.

FIG. 1 shows a block diagram of a computing system 100 that includes a computing platform 102 for establishing referrals within a referral network 104. System 100 includes a server 106 that is configured to implement various computing functions of platform 102 that are described herein. Platform 102 can be a predictive computing platform that includes datasets 108, scoring logic 114, and a machine learning (ML) system 116. System 100 may further include multiple computers, computing servers, and other computing devices that each include processors or processing devices and memory that stores compute logic or software/computing instructions that are executable by the processors. In some implementations, multiple computers can form a cluster of computing nodes or multiple node clusters that are used to perform the computational and/or machine learning processes described herein.

Server 106 is configured to access each of datasets 108, scoring logic 114, and ML system 116. In some implementations, ML system 116 and scoring logic 114 is included within server 106 as a sub-system of hardware circuits including one or more processor microchips. In general, server 106 can include one or more processors, memory, and data storage devices that collectively form one or more computing systems of server 106. Processors of the computing systems process instructions for execution by server 106, including instructions stored in the memory or on the storage device to display graphical information for a graphical user interface (GUI) on an example display of, for example, user device 104.

Execution of the stored instructions can cause one or more of the actions described herein to be performed by server 106 (or ML system 116). In other implementations, multiple processors may be used, as appropriate, along with multiple memories and types of memory. For example, server 106 may be connected with multiple other computing devices, with each device (e.g., a server bank, groups of servers, modules, or a multi-processor system) performing portions of the actions or operations associated with the various processes or logical flows described in this specification.

Datasets 108 can include one or more storage mediums that store datasets which include information about a variety of different controlled programs. For example, the information can describe entities that execute a variety of different programs (e.g., clinical trials or other controlled programs, including real-world and pragmatic programs). In some implementations, datasets 108 can indicate objectives that have been defined for different trial programs. The objectives can include Key Performance Indicators (KPIs) for assessing how well an entity or investigator performs a particular task that corresponds to a KPI. Information in datasets 108 indicate investigators (and providers) that are appropriately skilled to conduct (or support) trial programs based on a specialty of the entity (or provider) and an experience level of the investigator in conducting certain trial programs.

In some implementations, datasets 108 store information accessed by an example program management system (e.g., a clinical trial management system (CTMS)). For example, datasets 108 can be connected to an example CTMS that interacts with datasets 108 to retrieve, modify, and store information about multiple clinical trial programs. Hence, datasets 108 can include study attributes 110 that provide details about each of the multiple programs. For example, the details can include inclusion criteria specifying conditions for acceptance of a particular patient or subject into a trial program and exclusion criteria specifying conditions for exclusion of a particular patient from participation in a trial program. Datasets 108 can also include information pertaining to healthcare transactions. For example, datasets 108 can include information describing medical specialties of individual providers as well as transaction data describing health related interactions between patients and each of the multiple providers. Datasets 108 can also include information describing one or more connections that exist between investigators, healthcare providers, and public or private institutions (e.g., health care organizations, academic institutions, etc.).

Scoring logic 114 can be included in ML system 116 (described below) and is used to generate respective provider scores for one or more providers. For example, scoring logic 114 can be associated with an example score generator of system 100 that receives data values associated with a provider and generates a provider score based on the data values. Provider scores are used to characterize or assess referral attributes of a provider. Scoring logic 114 is configured to generate an initial provider score that indicates an initial or predicted assessment of the referral attributes of a provider. In some implementations, scoring logic 114 is a computing mechanism for recommending providers based on their referral attributes, forming provider tiers based on referral attributes, ranking providers based on referral attributes, or determining referral potential of a provider based on referral attributes. In addition, rather than a score (e.g., a numerical score), logic 114 can generate numerical parameters that represent a discrete recommendation metric, a provider tier relative to other providers, a provider's rank relative to other ranked providers, or a referral potential indicator for a specific provider.

As described in more detail below with reference to FIG. 3, scoring logic 114 interacts with an example analytics model to generate an adjusted provider score. The adjusted score can provide a more comprehensive assessment of a provider's referral attributes as well as a more accurate prediction of a provider's prospective referral activity. In some instances, provider scores generated by scoring logic 114 are produced using prediction data determined by ML system 116 based on analysis of data inputs from datasets 108. The data inputs may represent provider specific transaction information that can be used to infer or assess how well a provider will perform their referral activities within referral network 104.

A machine learning (ML) system 116 can be included within server 106 as a sub-system of hardware circuits that are programed to generate analytics model 118. For example, ML system 116 can include at least one neural network represented by a processor microchip that performs computations for generating learned inferences. Analytics model 118 can be generated based on learned inferences that result from iterative analysis of new and existing information included at datasets 108. For example, model 118 can interact with scoring logic 114 (e.g., by accessing the scoring logic) to execute certain predictive and analytical processes that are used to generate the adjusted provider scores (or the initial provider scores).

In some implementations, ML system 116 can be a dynamic recommendation engine that uses different sources of information accessed from datasets 108 to model connections between data describing healthcare activity, clinical trial programs, provider research, and educational materials. ML system 116 can generate an analytics model 118 that is configured to weight each connection based on the importance of the type of connection and a particular topic of interest. For example, model 118 can identify a topic of interest that corresponds to a trial program (e.g., an Alzheimer's treatment trial) and can weight a connection based on the importance of the type of connection using at least the respective provider score for a healthcare provider that specializes in treating patients with Alzheimer's.

Referral network 104 is generally formed by two or more entity client systems, user devices, or combinations of these systems and devices. For example, referral network 104 generally includes a first entity system 120 and a second entity system 126. Each of entity systems 120, 126 can include any known computer system, such as a desktop computer, a laptop computer, a tablet device, a mobile device, a smartphone, or any other related computing device configured to receive user input, exchange data communications with server 106, or exchange data communications with other computing systems.

Entity system 120 can be a computer system for a healthcare entity, such as a healthcare provider or a treating physician. Entity system 120 can store health data 122 that provides information about individuals that engage in healthcare related transactions with a provider that manages entity system 120. Health data 122 can include information about a variety of different patients, patient populations or patient groupings. In some implementations, assets of health data 122 are patient's electronic medical record (EMR), including EMR data inclusive of lab results, and other types of assets, such as claims data, prescription data, sales data for different treatment options, and lab data for different treatment options.

For example, a patient's EMR can provide a digital or electronic representation of the patient's hardcopy or paper medical chart and can include some or all information about the patient's medical history. In some implementations, health data 122 can include any information related to a patient's overall health, such as one or more medical conditions of the patient, or prescription therapies or pharmaceutical products being used by the patient. Analysis of health data 122 can be used to identify patient populations and other patient characteristics that are suitable candidates for participation in one or more clinical trial programs.

A computer system of entity system 120 can be configured to exchange data communications with platform 102 and entity system 126, via platform 102. For example, a display device of entity system 120 can generate a referral portal interface 124 that enables a provider to receive message communications generated by platform 102. As described in more detail below, at least one message communication can include an invitation or request to join referral network 104. Acceptance of the request to join referral network 104 enables a provider to refer one or more patients to an investigator for participation in a trial program. The provider can refer the one or more patients based on a referral connection that is established between the provider and an investigator that are each included in referral network 104.

Entity system 126 can correspond to a computer system for an entity that manages a program, such as a principal investigator that executes a clinical trial program at a particular geographic site location. Entity system 126 can store study data 128 that provides information about a clinical trial being executed by an investigator, such as information about patient volumes and other subjects that are tailored to particular study/trial program parameters. In some instances, study data 128 can include information that is similar (e.g., substantially similar) to study attributes 110, except that the information is specific to the clinical trial being executed by the investigator.

A computer system of entity system 126 can be configured to exchange data communications with platform 102 and with entity system 120, via platform 102. For example, a display device of entity system 126 can generate an investigator portal interface 130 that enables an investigator to receive message communications generated by platform 102. At least one message communication can indicate that a provider seeks to establish a referral connection with an investigator that manages entity system 126. Acceptance of the provider's request by the investigator forms an electronic referral connection that enables the provider to refer one or more patients to the investigator as candidates for participation in a trial program being executed by the investigator. Hence, the provider can refer the one or more patients to the investigator based on the referral connection that is established, via platform 102, between the provider and the investigator that are each connected in referral network 104.

Figure 2:
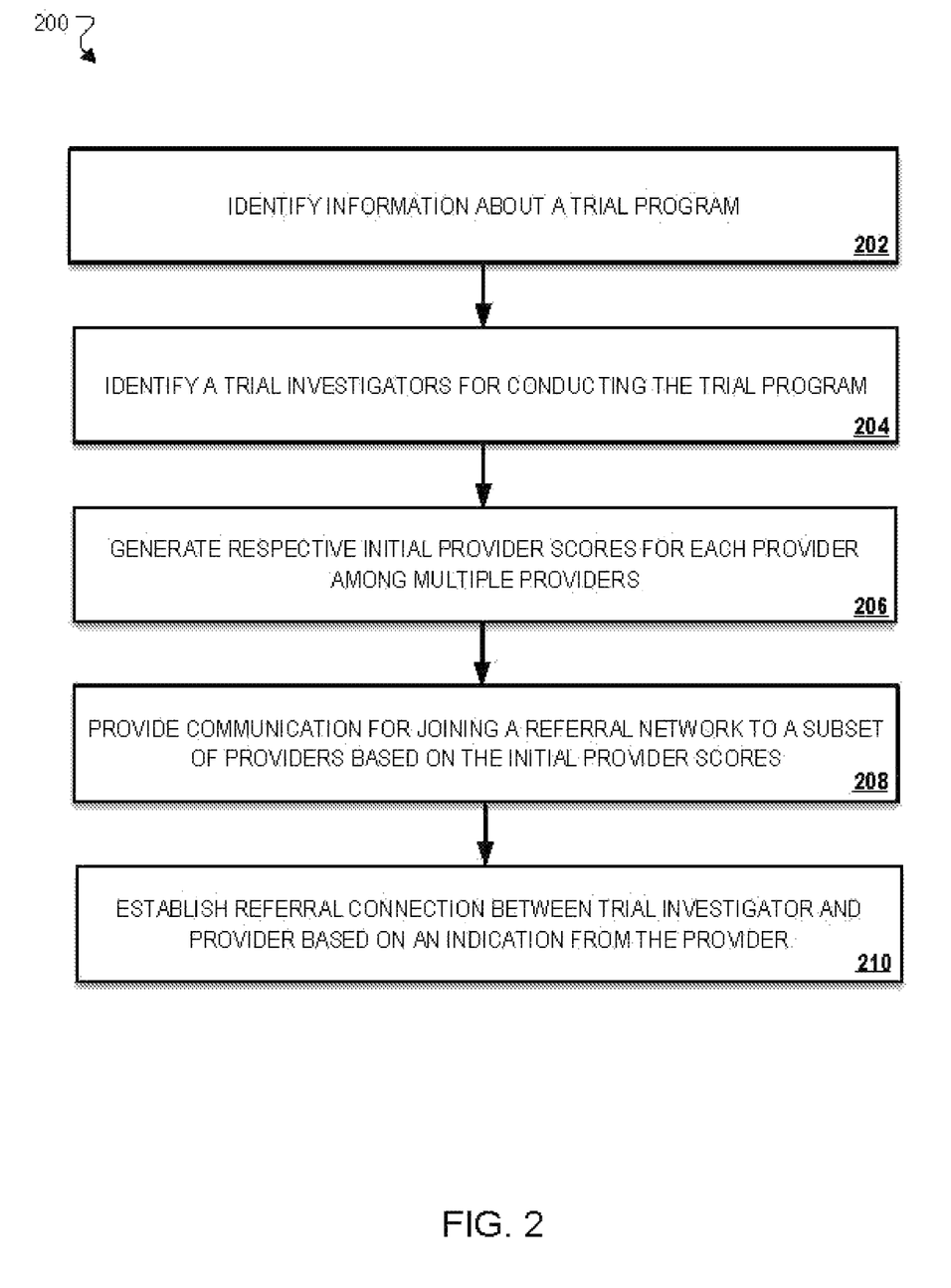
FIG. 2 shows an example process for establishing referral connections within a referral network.

FIG. 2 shows an example process 200 for establishing referral connections within a referral network. Process 200 can be implemented or executed using the systems described in this document. Thus, descriptions of process 200 may reference one or more of the above-mentioned computing resources of system 100. In some implementations, steps of process 200 are enabled by programmed instructions that executable by processing devices and memory of the systems described in this document.

Referring now to process 200, platform 102 identifies information about a trial program (202). The identified information is related to healthcare data included in datasets 108. For example, datasets 108 can include one or more data storage devices that each store various datasets for a clinical trial management system (CTMS). The datasets 108 can include information such as study attributes for multiple different clinical trial programs that are executed by different principal investigators. Additionally, the datasets can include medical specialty and treatment related information that is specific to multiple different healthcare providers. For example, the datasets can include information about an investigator's (or provider's) current participation in cancer treatment programs, heart disease treatment programs, Alzheimer's treatment programs, non-health related programs, or other distinct types of trial programs. In some implementations, information in datasets 108 can be used to determine how well provider might perform when asked to refer patients that suitable candidates for participation in trial program.

Platform 102 identifies an investigator based on the information about the trial program (204). For example, system can access datasets 108 and obtain program information associated with a clinical trial program that is identified in an example CTMS. The obtained information can be used to identify a particular investigator that specializes in executing the particular clinical trial program using one or more datasets that identify investigator by their trial specialty or prior trial experience.

Data analytics model 118 of platform 102 uses scoring logic 114 to generate a respective initial provider score for each provider from among multiple providers (206). For example, scoring logic 114 can be associated with an example score generator of system 100 that receives data values associated with at least one provider from analytics model 118. Scoring logic 114 generates a provider score based on the data values. For example, scoring logic 114 can generate the initial provider score based on at least one of: i) data values indicating a quantity of patients managed by the provider that are eligible for participation in the trial program; ii) data values indicating the provider's proximity to one or more of multiple trial investigators that specialize in conducting certain types of trial programs; or iii) data values indicating a quantity of patients managed by the provider that are shared with one or more of multiple trial investigators.

As indicated above, provider scores characterize or assess referral attributes of a provider and initial provider scores can provide a predicted assessment of the referral attributes of a provider. For example, initial provider scores for each provider in a subset indicates a predicted likelihood that the provider will identify and refer a patient or subject to a trial investigator that is a suitable candidate subject for participation in a trial program being executed by the investigator. Hence, the referral attributes are representative of a provider's propensity to proactively engage in referral activity and to refer suitable candidates based on the provider's eligible patient base and the provider's proximity to other trial investigators.

In some instances, initial provider scores might not provide the most comprehensive indicator of a provider's true potential for referring subjects that are likely to be ideal or even suitable candidates for participation in a trial program. As described in more detail below, adjusted provider scores can be generated to provide a more accurate assessment of provider's potential as a source for referral subjects that are suitable for participation in a trial program. As used in this document, subjects that are suitable for participation in a program include subjects that satisfy at least a threshold amount of conditions for participation that are specified by inclusion criteria described above.

In some implementations, generating the respective initial provider score for each provider includes generating a listing of providers that are identified for participation in the referral network 104. In addition, to generating the respective scores, scoring logic 114 can be used to rank each provider relative to other providers in the listing of providers. For example, scoring logic 114 can analyze the respective provider scores for each provider in the listing and rank each provider based on the analysis and accordance with a numerical indicator that represents that score. In some implementations, system 100 determines the subset of providers based on a ranking order of each provider in the listing or providers. In some instances, the multiple providers can form one or more groups or subsets of providers. Analytics model 118 generates the respective provider scores for each provider in a group based on analysis of the information in the stored as datasets 108. For example, the analyzed information of the datasets can include healthcare data that describes interactions between patients and healthcare providers in the group and criteria for the trial program.

Platform 102 provides a request to a subset of providers using the initial provider scores (208). For example, platform 102 is configured to provide, via server 106, an electronic request to each provider in a subset of providers based on the respective initial provider scores for each provider in the subset. Platform 102 provides the electronic request as a data communication that is received at entity system 120 and that is generated for display at referral portal interface 124. Where entity system 120 is associated with a healthcare provider, the electronic request can represent an invitation for the healthcare provider to join referral network 104.

Platform 102 is configured to establish a referral connection between the trial investigator and at least one healthcare provider in the subset of providers (210). For example, platform 102 uses the electronic request as a means to establish referral connections between multiple different trial investigators and particular types of healthcare providers in a subset of providers. The referral connections are established in response to platform 102 receiving an indication that a particular healthcare provider in the subset of providers has accepted the request to join referral network 104.

Figure 3:
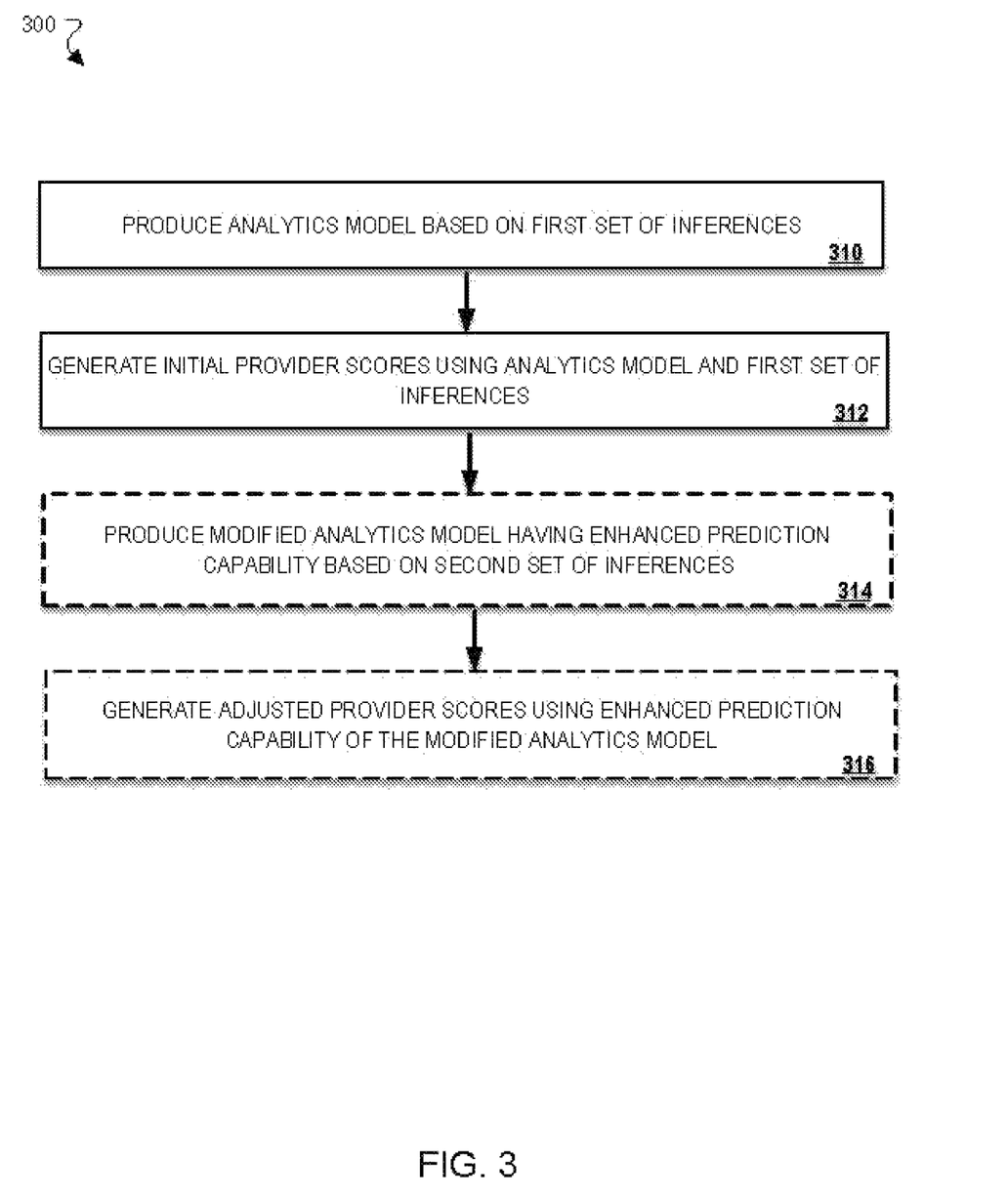
FIG. 3 shows an example process for enhancing the scoring logic used to establish referral connections within a referral network

FIG. 3 shows an example process 300 for generating initial provider scores and for enhancing scoring logic 114 used to establish referral connections within referral network 104. Similar to process 200, process 300 can be also implemented or executed using the systems described in this document. Hence, descriptions of process 300 may reference one or more of the above-mentioned computing resources of system 100 and steps of process 300 can be enabled by computing logic that is executable by processing devices and memory of the systems described in this document.

ML system 116 produces a data analytics model 118 based on a first set of inferences (310). For example, the first set of inferences can be determined from analysis of at least healthcare transaction data for each of the multiple providers or the inclusion and exclusion criteria specifying conditions for including subjects in, or excluding subjects from, a particular program. Analytics model 118 is generated based on the first set of inferences. These inferences can represent learned data connections (e.g., graph-based network connections) that resulted from iterative analysis of existing transaction data and criteria included at datasets 108. In some implementations, the first set of inferences are determined from analysis of various of other types of data, such as a provider's past or current clinical trial experience, a provider's medical research interest based on reviews of scientific and medical literature, a provider's education, a provider's workplace experience, and general medical and/or clinical trial surveys associated with different providers.

System 100 generates initial respective provider scores using the data analytics model 118 produced based on the first set of inferences (312). For example, analytics model 118 executes predictive and analytical processes to generate sets of data values related to certain characteristics of the provider, as discussed above. Analytics model 118 accesses scoring logic 114 and provides the data values as input parameters to the scoring logic. Scoring logic 114 processes the data values to generate the initial provider scores. The generated scores can be numerical scores, e.g., that range in value from 0.0-1.0, which provide a means for predicting a provider's prospective referral activities within network 104. As indicated above, rather than scores, logic 114 can generate numerical parameters (e.g., 1.0-10.0) that represent a discrete recommendation metric, a provider's tier relative to other providers, a provider's rank relative to other ranked providers, or a referral potential indicator for a specific provider. In some implementations, larger numerical values can correspond to a higher provider recommendation, a higher provider tier or provider rank, or a greater referral potential.

ML system 116 is configured to produce a modified data analytics model 118 that has enhanced prediction capability relative to an initial or baseline analytics model 118 (314). For example, a modified analytics model 118 can be generated based on new learned inferences that result from iterative analysis of new or modified information included at datasets 108. The new inferences can represent newly formed or adjusted data connections (e.g., graph-based network connections). The new or adjusted data connections can result from iterative analysis of data describing the referral activity for a provider that has been actively referring patients for a predetermined amount of time (e.g., one week, one month, or one year). For example, the data can indicate provider referral frequency (e.g., how often a provider initiates a referral), the types of subjects that are being referred by a provider, the quantity of referred subjects that match inclusion criteria of a program, or the quantify of referred subjects that are enrolled in a program and complete the trial program. Hence, the new inferences and new or adjusted data connections can over time function to enhance the prediction capabilities of analytics model 118 by identifying providers that engage in certain desired referral activities.

ML system 116 can use the modified data analytics model to generate a respective adjusted provider score using the enhanced prediction capability (316). The adjusted provider score can indicate an increased likelihood that a provider will identify and refer a patient to a trial investigator that is a suitable candidate for participation in a trial program being executed by the investigator. Conversely, the adjusted provider score can indicate a decreased likelihood that the provider will identify and refer a patient to the trial investigator that is a suitable candidate for participation in a trial program being executed by the investigator.

In some implementations, an adjusted provider score corresponds to a recommendation score/metric that can be referenced by an investigator when deciding whether to establish a referral connection with a provider. The recommendation metric can be based on data analyzed from different sources as well as the provider's past experiences in a patient referral process managed at platform 102. In some implementations, the recommendation metric takes into account the different types of overlapping data connections that can exist between entities (e.g., between providers, investigators, and institutions) and the quality of the connections. For example, the metric can be specific to available data about the entities and the data's relevance to a variety of different clinical trial specificities.

In some implementations, available data and the clinical trial specificities function to balance the different ways in which data values for generating a score (or metric) are weighted and can also cause scores to be adjusted in order to recommend providers that match (e.g., substantially match) the context of a provider's request for connection. For example, for a given set of clinical trial specificities, a provider score or metric of 0.8 (8.0) can indicate a provider that substantially matches, or at least matches, the context of a request for connection. In some implementations, the context of a request includes the type of clinical trial program, the specialty of the investigator that receives the request and that executes the trial program, the provider's eligible patient base, or the extent to which the provider's eligible patient base match the inclusion and exclusion criteria of the trial program.

Figure 4:
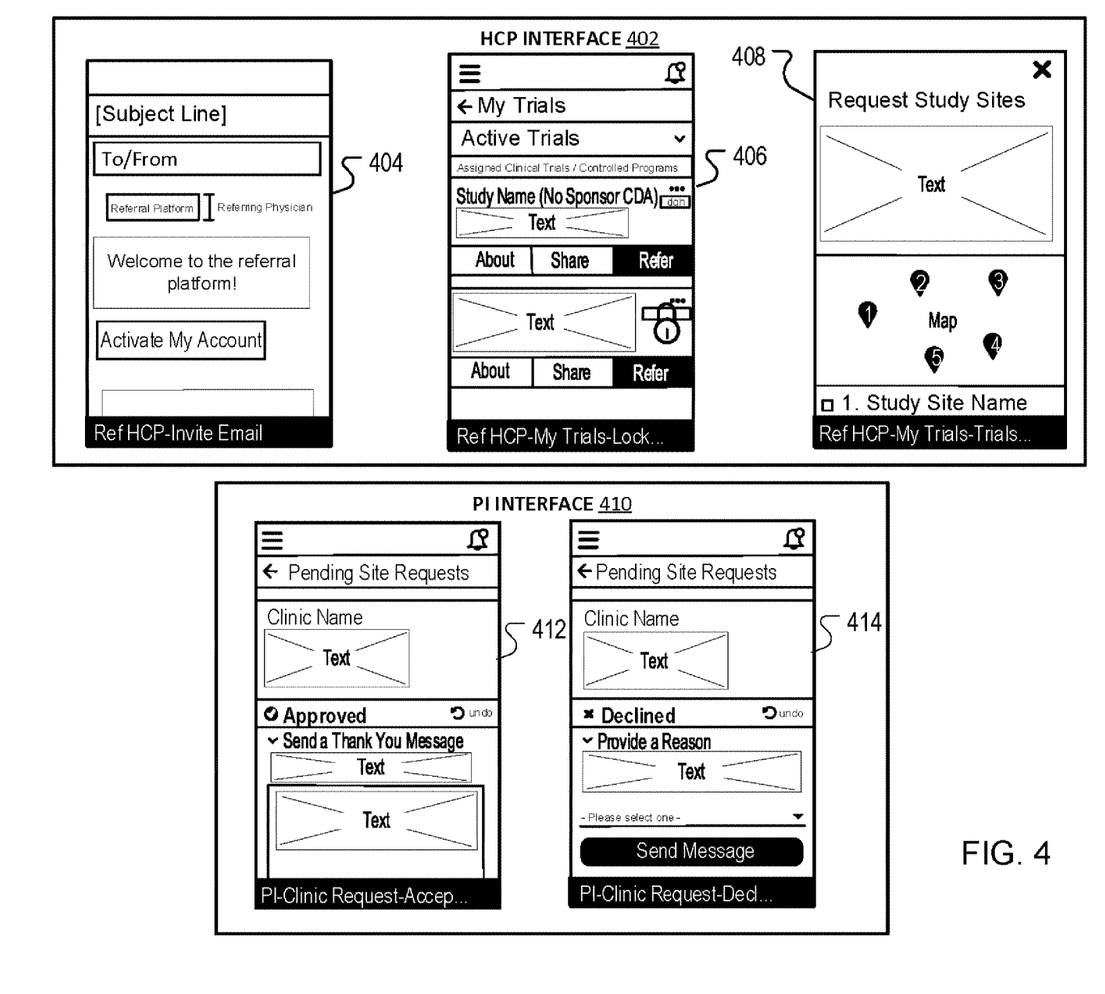
FIG. 4 shows graphical user interfaces that are generated using an application program of the referral network.

FIG. 4 shows graphical user interfaces that are generated using an application program managed at platform 102. Healthcare provider interface 402 corresponds to interface 124 described above with reference to FIG. 1, while principal investigator (PI) interface 410 corresponds to investigator interface 130 also described above with reference to FIG. 1. As shown at FIG. 4, interface 402 can include different graphical data 404, 406, and 408. Similarly, interface 410 can include different graphical data 412 and 414. Data 404 can represent an example interface that is generated when an identified provider receives a data communication about joining the electronic referral platform. For example, the communication can identify a particular trial program and can include an invitation or request for the provider to activate an account to begin the process of establishing referral connections with investigators and engaging in referral activity by referring subjects to the investigator.

Data 406 and 408 can represent information interfaces that respectively include active programs that are accessible by the provider (data 406) and information describing or identifying study sites/locations for the active programs (data 408). For example, data 408 can include text that informs a provider that, before engaging in referral activity (e.g., referring patients as subjects to a trial program occurring at a study site), the provider is required to send a request to a preferred study site. The text can also inform the provider that, after sending the request, the provider should receive either an acceptance, by an investigator, of the request or another indication, from the investigator, that is generally responsive to the request. Data 412 can represent an information interface that includes provider requests for establishing a referral connection that have been accepted by an investigator, while data 414 can represent an information interface that includes provider requests for establishing a referral connection that have been declined by an investigator.

Figure 5:
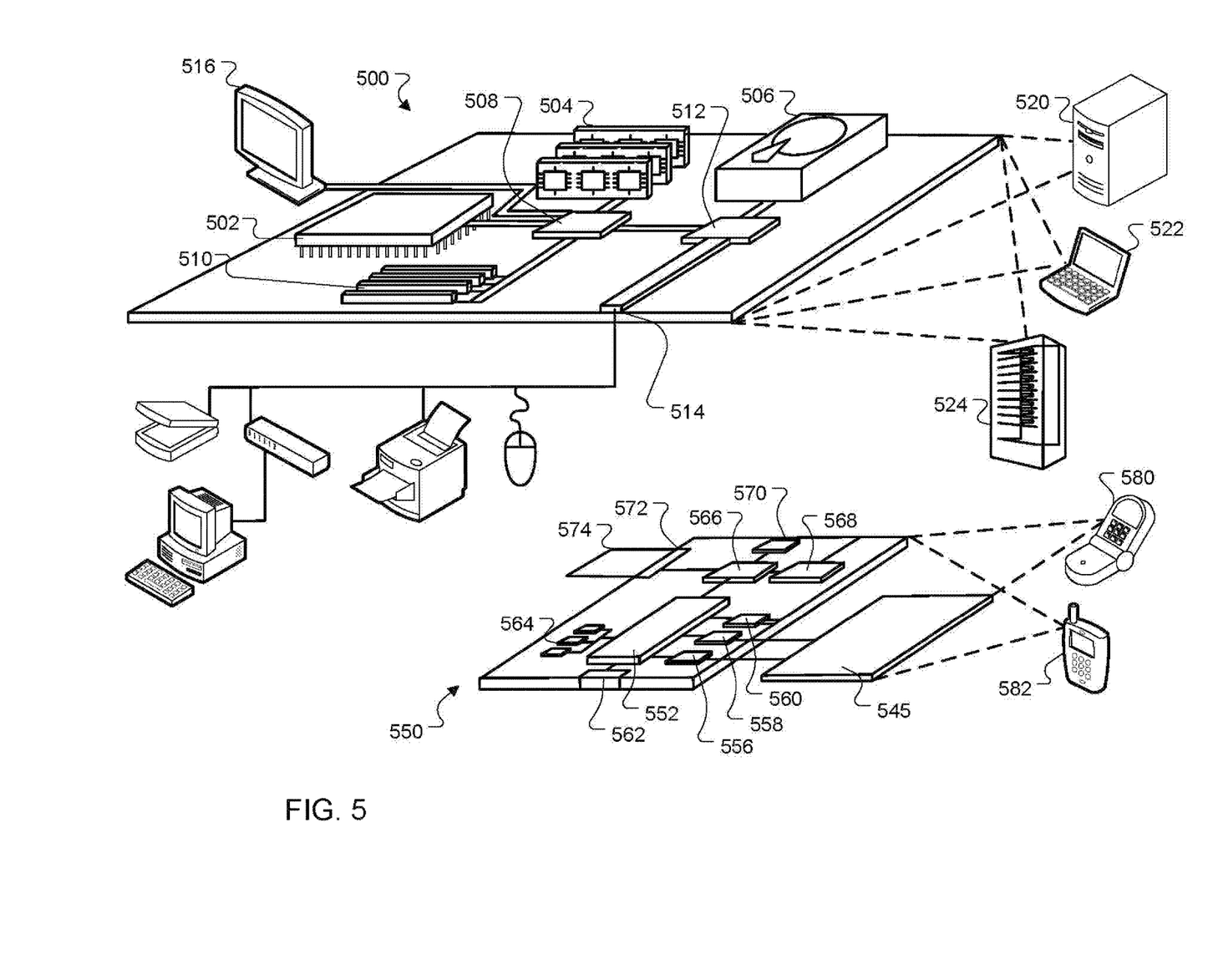
FIG. 5 shows a block diagram of a computing system that can be used in connection with computer-implemented methods described in this specification.

FIG. 5 is a block diagram of computing devices 500, 550 that may be used to implement the systems and methods described in this document, as either a client or as a server or plurality of servers. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, smartwatches, head-worn devices, and other similar computing devices. The components shown here, their connections and relationships, and their functions, are meant to be exemplary only, and are not meant to limit implementations described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations, e.g., as a server bank, a group of blade servers, or a multi-processor system.

The memory 504 stores information within the computing device 500. In one implementation, the memory 504 is a computer-readable medium. In one implementation, the memory 504 is a volatile memory unit or units. In another implementation, the memory 504 is a non-volatile memory unit or units.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516, e.g., through a graphics processor or accelerator, and to high-speed expansion ports 510, which may accept various expansion cards (not shown). In the implementation, low-speed controller 512 is coupled to storage device 506 and low-speed expansion port 514. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may include appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication, e.g., via a docking procedure, or for wireless communication, e.g., via Bluetooth or other such technologies.

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a SIMM card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provided as a security module for device 550, and may be programmed with instructions that permit secure use of device 550. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound, e.g., voice messages, music files, etc., and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

The invention claimed is:

1. A computer-implemented method, comprising:
   determining, using a predictive analytics model implemented on a hardware circuit, prospective patient referral activity of a provider based on data describing healthcare interactions between patients and the provider;
   determining, based on numerical parameters computed at the hardware circuit using the predictive analytics model, weighted connections between information about a clinical trial and the data describing the healthcare interactions;
   iteratively computing, by the predictive analytics model, machine-learning inferences to enhance, based on the weighted connections, a capability of the predictive analytics model to accurately predict prospective patient referral activity of different providers;
   generating, using the enhanced predictive capability of the predictive analytics model, an adjusted score representing a predicted likelihood at least one of the different providers will refer candidates to a trial investigator that conducts the clinical trial;
   based on the adjusted score, establishing a referral connection between the trial investigator and the provider that enables a patient referral from the provider to the trial investigator; and
   generating, using the referral connection, a referral output identifying a patient for participation in the clinical trial based on data communications between the provider and the trial investigator.

2. The method of claim 1, comprising:
   generating a respective adjusted score for each provider in a listing of providers that are identified for participation in an electronic referral network.

3. The method of claim 2, wherein generating the respective adjusted score for each provider in the listing of providers comprises:
   generating the respective adjusted score based on at least one of:
   a quantity of patients managed by the provider that are eligible for participation in the clinical trial;
   a proximity of the provider relative to one or more of multiple trial investigators conducting the clinical trial; or
   a quantity of patients managed by the provider that are shared with one or more of multiple trial investigators conducting the clinical trial.

4. The method of claim 3, comprising:
   producing, by training a neural network of a machine learning system, the predictive analytics model based on a first set of inferences determined using the neural.

5. The method of claim 4, further comprising:
   enhancing a predictive capability of the predictive analytics model based on a of machine-learning inferences computed by the machine learning system using the neural network; and generating the respective adjusted score for each provider in the subset of providers using the enhanced prediction capability of the predictive analytics model.

6. The method of claim 5, wherein the respective adjusted score for each provider in the subset indicates:
an increased likelihood that the provider will identify and refer, to the trial investigator, a candidate that satisfies particular criteria for participation in the clinical trial.

7. The method of claim 4, wherein criteria for the clinical trial comprises:
inclusion criteria for identifying candidate subjects for participation in the clinical trial; and
exclusion criteria for identifying candidate subjects to be excluded from participating in the clinical trial.

8. A system, comprising:
one or more processing devices; and
one or more non-transitory machine-readable storage devices storing instructions that are executable by the one or more processing devices to cause performance of operations comprising:
determining, using scoring logic and a predictive analytics model implemented on a hardware circuit, prospective patient referral activity of a provider based on data describing healthcare interactions between patients and the provider;
determining, based on numerical parameters computed at the hardware circuit using the predictive analytics model, weighted connections between information about a clinical trial and the data describing the healthcare interactions;
iteratively computing, by the predictive analytics model, machine-learning inferences to enhance, based on the weighted connections, a capability of the predictive analytics model to accurately predict prospective patient referral activity of different providers;
generating, using the enhanced predictive capability of the predictive analytics model, an adjusted score representing a predicted likelihood at least one of the different providers will refer candidates to a trial investigator that conducts the clinical trial;
based on the adjusted score, establishing a referral connection between the trial investigator and the provider that enables a patient referral from the provider to the trial investigator; and
generating, using the referral connection, a referral output identifying a patient for participation in the clinical trial based on data communications between the provider and the trial investigator.

9. The system of claim 8, wherein the operations comprise:
generating a respective adjusted score for each provider in a listing of providers that are identified for participation in an electronic referral network.

10. The system of claim 9, wherein generating the respective adjusted score for each provider in the listing of providers comprises:
generating the respective adjusted score based on at least one of:
a quantity of patients managed by the provider that are eligible for participation in the clinical trial;
a proximity of the provider relative to one or more of multiple trial investigators conducting the clinical trial; or
a quantity of patients managed by the provider that are shared with one or more of multiple trial investigators conducting the clinical trial.

11. The system of claim 10, wherein the operations comprises:
producing, by training a neural network of a machine learning system, the predictive analytics model based on a first set of inferences determined using the neural.

12. The system of claim 11, wherein the operations further comprise:
enhancing a predictive capability of the predictive analytics model based on a set of machine-learning inferences computed by the machine learning system using the neural network; and
generating the respective adjusted score for each provider in the subset of providers using the enhanced prediction capability of the predictive analytics model.

13. The system of claim 12, wherein the respective adjusted score for each provider in the subset indicates:
an increased likelihood that the provider will identify and refer, to the trial investigator, a candidate that satisfies particular criteria for participation in the clinical trial.

14. The system of claim 11, wherein criteria for the clinical trial comprises:
inclusion criteria for identifying candidate subjects for participation in the clinical trial; and
exclusion criteria for identifying candidate subjects to be excluded from participating in the clinical trial.

15. One or more non-transitory machine-readable storage devices storing instructions that are executable by one or more processing devices to cause performance of operations comprising:
determining, using a predictive analytics model implemented on a hardware circuit, prospective patient referral activity of a provider based on data describing healthcare interactions between patients and the provider;
determining, based on numerical parameters computed at the hardware circuit using the predictive analytics model, weighted connections between information about a clinical trial and the data describing the healthcare interactions;
iteratively computing, by the predictive analytics model, machine-learning inferences to enhance, based on the weighted connections, a capability of the predictive analytics model to accurately predict prospective patient referral activity of different providers;
generating, using the enhanced predictive capability of the predictive analytics model, an adjusted score representing a predicted likelihood at least one of the different providers will refer candidates to a trial investigator that conducts the clinical trial;
based on the adjusted score, establishing a referral connection between the trial investigator and the provider that enables a patient referral from the provider to the trial investigator; and
generating, using the referral connection, a referral output identifying a patient for participation in the clinical trial based on data communications between the provider and the trial investigator.

16. The machine-readable storage device of claim 15, wherein the operations comprise:
generating a respective adjusted score for each provider in a listing of providers that are identified for participation in an electronic referral network.

17. The machine-readable storage device of claim 16, wherein generating the respective adjusted score for each provider in the listing of providers comprises:
generating the respective adjusted score based on at least one of:

a quantity of patients managed by the provider that are eligible for participation in the clinical trial;

a proximity of the provider relative to one or more of multiple trial investigators conducting the clinical trial; or a quantity of patients managed by the provider that are shared with one or more of multiple trial investigators conducting the clinical trial.

18. The method of claim 4, comprising:

establishing, between the trial investigator and a corresponding provider in the subset, a referral connection that enables a respective patient referral from the corresponding provider to the trial investigator.

19. The method of claim 4, wherein the predictive analytics model represents a dynamic recommendation engine.

20. The system of claim 11, wherein the predictive analytics model represents a dynamic recommendation engine.

\* \* \* \* \*

UNITED STATES PATENT AND TRADEMARK OFFICE
CERTIFICATE OF CORRECTION

| | | |
|---|---|---|
| PATENT NO. | : 11,189,364 B1 | Page 1 of 1 |
| APPLICATION NO. | : 15/914653 | |
| DATED | : November 30, 2021 | |
| INVENTOR(S) | : Katie Shaw et al. | |

It is certified that error appears in the above-identified patent and that said Letters Patent is hereby corrected as shown below:

On the Title Page

Item [57], Line 14, delete "to for" and insert --for--.

In the Claims

Column 16, Line 65, Claim 5, after "a" insert --set--.

Column 17, Line 22, Claim 8, after "using" delete "scoring logic and".

Column 18, Line 10, Claim 12, after "by the", delete "machine learning" and insert --machine-learning--.

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*